United States Patent
Reed et al.

(10) Patent No.: US 11,678,982 B2
(45) Date of Patent: Jun. 20, 2023

(54) REPLACEMENT HEART VALVE ASSEMBLY WITH A VALVE LOADED DISTALLY FROM A STENT

(71) Applicant: Anteris Technologies Corporation, Eagan, MN (US)

(72) Inventors: Andrew Reed, Eagan, MN (US); Dave Mathieu, Eagan, MN (US); Philip J. Haarstad, Eagan, MN (US); Alex A. Peterson, Eagan, MN (US); William Morris Leonard Neethling, Eagan, MN (US); Tuan Doan, Eagan, MN (US); Christopher P. Olig, Eagan, MN (US); Scott Bliss, Eagan, MN (US)

(73) Assignee: Anteris Technologies Corporation, Eagan, MN (US)

( * ) Notice: Subject to any disclaimer, the term of this patent is extended or adjusted under 35 U.S.C. 154(b) by 0 days.

(21) Appl. No.: 17/056,006

(22) PCT Filed: May 20, 2019

(86) PCT No.: PCT/US2019/033167
§ 371 (c)(1),
(2) Date: Nov. 17, 2020

(87) PCT Pub. No.: WO2019/222756
PCT Pub. Date: Nov. 21, 2019

(65) Prior Publication Data
US 2021/0212823 A1    Jul. 15, 2021

Related U.S. Application Data

(60) Provisional application No. 62/673,221, filed on May 18, 2018, provisional application No. 62/674,878, filed on May 22, 2018.

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/95* (2013.01); *A61F 2/2433* (2013.01); *A61F 2002/9534* (2013.01)

(58) Field of Classification Search
CPC ........ A61F 2/2436; A61F 2/2418; A61F 2/95; A61F 2/2433; A61F 2002/9534;
(Continued)

(56) References Cited

U.S. PATENT DOCUMENTS 4,624,822 A    11/1986 Arru et al.
6,491,511 B1   12/2002 Duran et al.
(Continued)

FOREIGN PATENT DOCUMENTS

CN    203736349        7/2014
EP    2777618 A1       9/2014
(Continued)

OTHER PUBLICATIONS

Knee Hiang Lim et al., Flat or Curved Pericardial Aortic Valve Cusps: A Finite Element Study, Journal of Heart Valve, vol. 13, No. 5 (Sep. 2004).
(Continued)

*Primary Examiner* — Suzette J Gherbi

(57) ABSTRACT

A replacement heart valve assembly where the valve is loaded into the catheter distally, and separately from the stent. The valve has a locking member and the stent has a locking channel. Once in the expanded position, the valve is pulled towards the stent until the locking member is engaged with the locking channel.

13 Claims, 6 Drawing Sheets

(58) Field of Classification Search
CPC ...... A61F 2220/0025; A61F 2220/0033; A61F 2250/006
See application file for complete search history.

(56) References Cited

U.S. PATENT DOCUMENTS

| | | | |
|---|---|---|---|
| 6,682,559 B2 | 1/2004 | Myers et al. | |
| 7,025,780 B2 | 4/2006 | Gabbay | |
| 7,087,079 B2 | 8/2006 | Navia et al. | |
| 8,778,018 B2 | 7/2014 | Iobbi | |
| 9,011,525 B2 | 4/2015 | Claiborne, III et al. | |
| 9,095,430 B2 | 8/2015 | Cunanan et al. | |
| 9,192,470 B2 | 11/2015 | Cai et al. | |
| 9,205,172 B2 | 12/2015 | Neethling et al. | |
| 9,259,313 B2 | 2/2016 | Wheatley | |
| 9,301,835 B2 | 4/2016 | Campbell et al. | |
| 9,554,902 B2 | 1/2017 | Braido et al. | |
| 9,744,037 B2* | 8/2017 | Kheradvar | A61F 2/2418 |
| 9,763,780 B2 | 9/2017 | Morriss et al. | |
| 11,135,059 B2* | 10/2021 | Hammer | A61F 2/2409 |
| 11,464,635 B2* | 10/2022 | Reimer | A61F 2/2418 |
| 2003/0069635 A1 | 4/2003 | Cartledge et al. | |
| 2005/0123582 A1 | 6/2005 | Sung et al. | |
| 2005/0137687 A1 | 6/2005 | Salahieh et al. | |
| 2005/0240262 A1 | 10/2005 | White | |
| 2006/0020327 A1 | 1/2006 | Lashinski et al. | |
| 2008/0288055 A1 | 11/2008 | Paul, Jr. | |
| 2010/0049313 A1 | 2/2010 | Alon et al. | |
| 2011/0066224 A1 | 3/2011 | White | |
| 2011/0238167 A1 | 9/2011 | Dove et al. | |
| 2012/0277855 A1 | 11/2012 | Lashinski et al. | |
| 2013/0018458 A1 | 1/2013 | Yohanan et al. | |
| 2013/0184811 A1 | 7/2013 | Rowe et al. | |
| 2013/0204360 A1 | 8/2013 | Gainor | |
| 2013/0310927 A1 | 11/2013 | Quintessenza | |
| 2014/0005772 A1 | 1/2014 | Edelman et al. | |
| 2014/0031924 A1 | 1/2014 | Bruchman et al. | |
| 2014/0277417 A1 | 9/2014 | Schraut et al. | |
| 2014/0324160 A1 | 10/2014 | Benichou et al. | |
| 2015/0134056 A1* | 5/2015 | Claiborne, III | A61F 2/2412 623/2.11 |
| 2015/0142104 A1 | 5/2015 | Braido | |
| 2015/0209141 A1 | 7/2015 | Braido et al. | |
| 2015/0216663 A1 | 8/2015 | Braido et al. | |
| 2015/0320556 A1 | 11/2015 | Levi et al. | |
| 2016/0128831 A1* | 5/2016 | Zhou | A61F 2/966 623/2.11 |
| 2016/0135951 A1* | 5/2016 | Salahieh | A61F 2/2427 623/2.11 |
| 2016/0143732 A1 | 5/2016 | Glimsdale | |
| 2016/0158007 A1 | 6/2016 | Centola et al. | |
| 2016/0175095 A1 | 6/2016 | Dienno et al. | |
| 2016/0220365 A1 | 8/2016 | Backus et al. | |
| 2016/0317293 A1 | 11/2016 | Matheny et al. | |
| 2016/0331532 A1 | 11/2016 | Quadri | |
| 2016/0367360 A1 | 12/2016 | Cartledge et al. | |
| 2016/0367364 A1 | 12/2016 | Torrianni et al. | |
| 2017/0049566 A1 | 2/2017 | Zeng et al. | |
| 2017/0056170 A1* | 3/2017 | Zhu | A61F 2/958 |
| 2017/0119525 A1 | 5/2017 | Rowe et al. | |
| 2017/0189174 A1 | 7/2017 | Braido et al. | |
| 2017/0312075 A1 | 11/2017 | Fahim et al. | |
| 2018/0028312 A1 | 2/2018 | Fhill et al. | |
| 2018/0228603 A1* | 8/2018 | Racchini | A61F 2/2412 |
| 2019/0117390 A1 | 4/2019 | Neethling et al. | |
| 2021/0212819 A1 | 7/2021 | Reed et al. | |
| 2021/0212822 A1 | 7/2021 | Reed et al. | |
| 2021/0212823 A1 | 7/2021 | Reed et al. | |

FOREIGN PATENT DOCUMENTS

| | | |
|---|---|---|
| EP | 3697343 | 8/2020 |
| JP | 2008-264553 | 11/2008 |
| JP | 2015519187 A | 7/2015 |
| WO | 2001076510 A2 | 10/2001 |
| WO | 2003/030776 | 4/2003 |
| WO | 2007013999 A2 | 2/2007 |
| WO | 2011072084 A2 | 6/2011 |
| WO | 2011109450 A2 | 9/2011 |
| WO | 2014204807 A1 | 12/2014 |
| WO | 2015126712 A1 | 8/2015 |
| WO | 2015173794 A1 | 11/2015 |
| WO | 2017031155 A1 | 2/2017 |

OTHER PUBLICATIONS

Search Report and Written Opinion for related PCT Application No. PCT/US2019/033167 dated Sep. 3, 2019 (9 pages).

\* cited by examiner

REPLACEMENT HEART VALVE ASSEMBLY WITH A VALVE LOADED DISTALLY FROM A STENT

CROSS-REFERENCE TO RELATED APPLICATIONS

The present disclosure claims priority to Provisional Application No. 62/673,221, and filed May 18, 2018, and to U.S. Provisional Application No. 62/674,878, filed May 22, 2018, entitled "Replacement Heart Valve Assembly With a Valve Loaded Distally From a Stent", the contents of which are hereby incorporated by reference herein in their entirety.

FIELD OF THE INVENTION

The present disclosure relates to novel and advantageous devices and methods for a transcatheter valve replacement devices.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Native heart valves may need to be replaced when a patient has a condition such as congenital heart defect or valvular heart disease. A diseased heart valve may result in regurgitation, where the valve is not properly function and blood flows in a direction opposite the normal direction of the flow, and/or stenosis, where the valve has narrowed through in some instances calcification of the valve, some obstruction of the valve such as plaque, or inflammation. Heart valves may be replaced through surgical repair or a valve deployed relative to the native heart valve through a transcatheter approach. Transcatheter valve replacement devices generally comprise leaflets of tissue that are attached to an expandable or self-expanding stent construct that is crimped onto a catheter for deployment. The stent is advanced to the location of the troubled heart valve, where it expands or is expanded by a balloon or other means. Once seated in the valve, blood flow and the muscles of the heart will result in the tissue leaflets to open and close.

One challenge affecting transcatheter valve replacement devices is the French size of the catheter required to deliver the valve replacement device to the affected native heart valve through the vasculature. There is a desire to reduce the French size of the catheter to improve maneuverability of the catheter as it is advanced to the site of the affected native heart valve.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

In at least one embodiment of the present disclosure, a system for endovascular heart valve repair comprises a delivery catheter and a valve assembly. The delivery catheter may comprise a retractable sheath and an inner shaft coaxial with the retractable sheath. In a delivery position, the valve assembly may be disposed between the retractable sheath and the inner shaft in a delivery position. The valve assembly may comprise a stent and a valve, which may be positioned within the catheter separately from the valve in a delivery position. The stent may have a proximal end and a distal end. The stent may have an outer surface and an inner surface defining a stent lumen. The stent may have at least one locking channel. The valve may have a proximal end and a distal end. The valve may have an outer surface and an inner surface defining a valve lumen. The valve may further comprise at least one valve leaflet within the valve lumen. The valve may further comprise a valve body that extends from the proximal end to the distal end. The valve may further comprise a cuff at the distal end of the cuff and a valve channel defined between the cuff and the valve body's outer surface. The valve may also comprise at least one valve locking feature for engagement with the at least one locking channel on the stent. In some embodiments, when the valve assembly is in an expanded position, the valve is moved in a proximal direction towards the distal end of the stent until the valve locking feature is engaged with the locking channel and the distal end of the stent is positioned within the valve channel. In some embodiments, the valve locking feature may be positioned within the valve channel. In some embodiments, the system may further comprise at least one cable wire disposed between the retractable sheath and the inner shaft to assist with pulling the valve towards the stent. In some embodiments, a distal end of the at least one cable wire is connected to the valve. The at least one cable wire may be connected to the distal end of the valve. The at least one cable wire may be connected to the valve locking feature.

In at least one embodiment, a replacement valve may comprise a valve body having a proximal end and a distal end, the valve body having an outer surface and an inner surface defining a valve lumen; at least one valve leaflet within the valve lumen; a cuff at the distal end of the valve and overlapping a portion of the valve body at a distal end of the cuff; a valve channel between the cuff an outer surface of the valve body; and at least one valve locking feature. In some embodiments, the at least one valve locking feature is disposed within the valve channel. In some embodiments, the at least one valve locking feature is positioned on an outer surface of the valve body. In other embodiments, the at least one valve locking feature is positioned on the inner surface of the valve.

In at least one embodiment, the replacement heart valve assembly comprises a stent and a valve. The stent may have a proximal end and a distal end. The stent may have an outer surface and an inner surface defining a stent lumen. The stent may have a proximal end and a distal end. The stent may have an outer surface and an inner surface defining a stent lumen. The stent may have at least one locking channel. The valve may have a proximal end and a distal end. The valve may have an outer surface and an inner surface defining a valve lumen. The valve may further comprise at least one valve leaflet within the valve lumen. The valve may further comprise a valve body that extends from the proximal end to the distal end. The valve may further comprise a cuff at the distal end of the cuff and a valve channel defined between the cuff and the valve body's outer surface. The valve may also comprise at least one valve locking feature for engagement with the at least one locking channel on the stent to fully deploy the stent.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure relates to replacement heart valves for use in the mitral valve, tricuspid valve, aortic valve or pulmonary valve of the heart. In some circumstances, a replacement heart valve may be disposed within the native valve such that portions of the replacement heart valve, or portions of a device such as a stent attached to the replacement heart valve, are adjacent to the native heart valve.

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion. Although this application uses the terms "proximal" and "distal" in the same relative manner with respect to the devices shown in the figures, it is within the scope of this invention that "proximal" and "distal" can be interchanged with "distal" and "proximal" in other embodiments.

In prior valve replacement devices, the valve assembly is loaded within a catheter assembly with the valve wrapped inside the stent's lumen, and, in some instances, the valve is even wrapped about a balloon within the stent's lumen for balloon-expandable stents. This creates a significant thickness of the valve assembly in the delivery position. Thus, a larger French size of the catheter assembly needed to deliver deploy the valve. Larger French sizes and thicker sections reduce flexibility and eliminate potential entry points in the vasculature due to size of the catheter necessary to deliver and deploy the valve. The embodiments of this invention reduce the thickness of the valve assembly in the delivery position to enable a reduction in the French size of the catheter needed for delivery of the valve assembly to a valve repair site.

Figure 1:
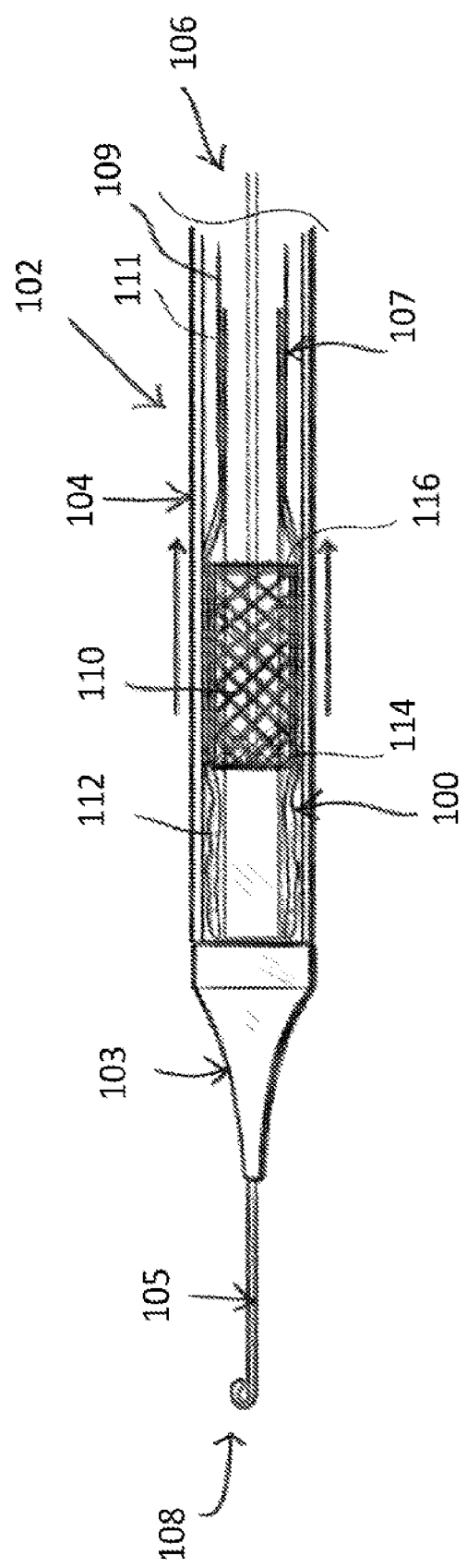
FIG. 1 is a side view of one embodiment of a replacement heart valve assembly disposed within the retractable sheath of a catheter in a delivery position.
Figure 2:
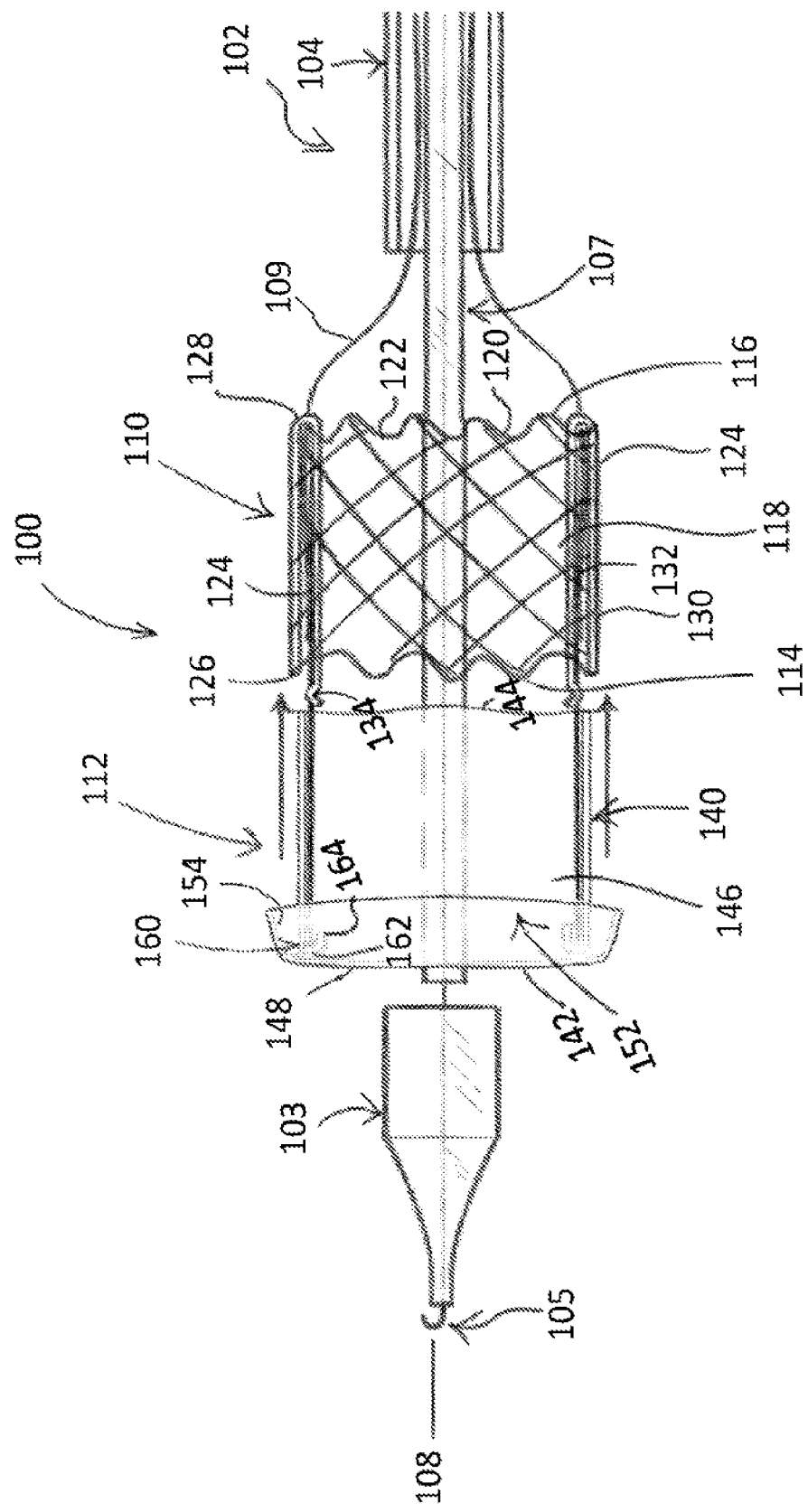
FIG. 2 is a side view of the replacement heart valve assembly of FIG. 1 in an expanded position.
Figure 3:
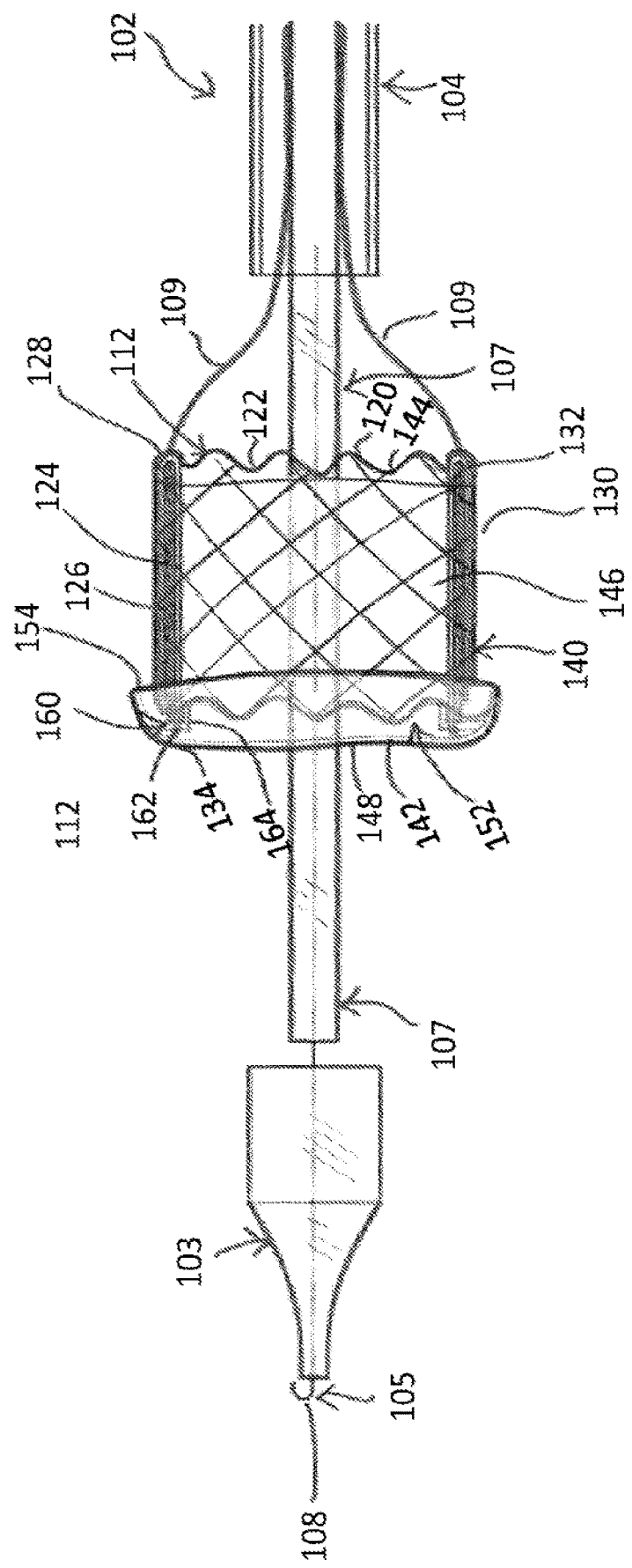
FIG. 3 is a side view of the replacement heart valve assembly of FIG. 2 in a deployed position, with the valve in an engaged position with the stent of the replacement heart valve assembly.

FIGS. 1-3 show an embodiment of the present disclosure. FIG. 1 shows a valve assembly 100 of the present disclosure loaded within a catheter assembly 102 in a delivery position. FIGS. 2-3 show the valve assembly in an expanded position. The valve assembly 100 comprises a stent 110 and a valve 112 disposed generally distally of the stent 110. In at least one embodiment, the stent 110 is not directly connected to the valve 112. In at least one embodiment, the valve 112 is loaded separately from the stent. By having the valve 112 disposed generally distally of the stent in the delivery position, this reduces the size of the catheter needed for delivery of the valve assembly to a valve repair site.

The valve 112 may comprise a tissue material. The valve 112 may be constructed, in some embodiments, from a single piece of tissue material. In some embodiments, the tissue material is an implantable biomaterial such as the biomaterial described in the disclosure of U.S. Patent Provisional App. Ser. No. 62/574,410 filed on Oct. 19, 2017 and entitled "Replacement Heart Valve with Reduced Suturing," which is incorporated by reference herein in its entirety. In other embodiments, the valve 112 may be constructed from multiple pieces of tissue material. In some embodiments, the tissue material may be a biomaterial. In some embodiments, the tissue material may be a cross-linked collagen based-biomaterial that comprises acellular or cellular tissue selected from the group consisting of cardiovascular tissue, heart tissue, heart valve, aortic roots, aortic wall, aortic leaflets, pericardial tissue, connective tissue, dura mater, dermal tissue, vascular tissue, cartilage, pericardium, ligament, tendon, blood vessels, umbilical tissue, bone tissue, fasciae, and submucosal tissue and skin. In some embodiments, the tissue material is an implantable biomaterial such as the biomaterial described in the disclosure of U.S. Pat. No. 9,205,172, filed on Dec. 21, 2005 and entitled "Implantable Biomaterial and Method of Producing Same," which is incorporated by reference herein in its entirety. In some embodiments, the tissue material may be artificial tissue. In some embodiments, the artificial tissue may comprise a single piece molded or formed polymer. In some embodiments, the artificial tissue may comprise polytetrafluoroethylene, polyethylene terephthalate, other polymers, and other polymer coatings.

The catheter assembly 102 has a retractable sheath 104 with a proximal end 106 and a distal end 108. The catheter assembly 102 may further comprise a tip 103 near the distal end 108, a guidewire 105, and an inner shaft 107 coaxial with the retractable sheath 104. The guidewire 105 may be disposed within the inner shaft 107. The catheter assembly 102 may comprise at least one locking wire 109 connected to the valve assembly 100 for pulling the valve 112, in an expanded position, in a proximal direction towards the stent 110 also in an expanded position to connect the stent to the valve 112. The at least one locking wire 109 may be positioned between the inner shaft 107 and the retractable sheath 104. As shown in FIG. 1, the catheter assembly 102 has at least two locking wires 109, although it is contemplated by this disclosure that any number of locking wires 109 may be suitable to control the engagement of the valve 112 with the stent 110.

The stent 110 may be a balloon expandable, self-expanding, or otherwise expandable stent capable of expanding from a delivery position to a deployed position. The stent 110 may comprise Nitinol or any other suitable material for the stent. As shown on FIGS. 1-3, the stent 110 has a distal end 114, a proximal end 116, an outer surface 118 extending between the distal end 114 and the proximal end 116, and an inner surface 120 extending between the distal end 114 and the proximal end 116 and defining a stent lumen 122 therein.

The stent 110 further comprises at least one stent locking feature 124 configured to receive at least a portion of the valve. In some embodiments, the locking channel may be a track, a wire, opening within the stent, a feature of a strut of the stent, or another element for connecting with a mating feature on the valve to engage the valve with the stent. As shown, the stent may comprise two stent locking features 124, which are shown as channels. The stent may comprise any number of stent locking features 124, but in some embodiments the stent has the same number of stent locking features 124 as there are commissures on the valve. Where the stent locking features 124 are positioned at the commissures of the valve, the stent locking features may provide additional support to these areas of the valve. The stent locking feature 124, which is shown as a channel, may extend axially along the length of the stent 110 from the distal end 114 to the proximal end 116. At least in the embodiment shown, the stent locking feature 124 may comprise an open end 126 at the distal end 114 of the stent 110 and a closed end 128 at the proximal end 116 of the stent 110. In some embodiments, as shown the locking wire 109 may extend at least partially through the locking channel 124 to the valve 112. The stent locking feature 124 may have a first side 130 and a second side 132, where the first side 130 abuts the inner surface 120 of the stent 110. The second side 132 may extend into the stent lumen 122. The stent locking feature 124 may have a flanged portion 134 near the open end 126 to guide the engagement of the valve 112 with the stent 110 and also engage with the locking feature of the valve. In some embodiments, the stent locking feature 124 may incorporate a radiopaque marker or other imaging marker to assist with proper positioning of the stent. More particularly the flanged portion may, in some embodiments, incorporate a radiopaque marker or other imaging marker to assist with proper positioning of the stent.

The valve 112 may comprise a valve body 140 defining a distal end 142, a proximal end 144, an outer surface 146 extending between the distal end 142 and the proximal end 144, and an inner surface 148 extending between the distal end 124 and the proximal end 126. The inner surface 148 may define a valve lumen. At least one valve leaflet may be disposed with the valve lumen. The valve 112 may further comprise a number of commissures, which may or may not be equal to the number of valve leaflets of the valve 112. In at least one embodiment, the valve 112 may have three leaflets and three commissures. The valve 112 may further comprise a cuff 152 near the distal end 142 of the valve body. The cuff 152 defines a valve channel 154 between the cuff 152 and the outer surface 146 of the valve body 140. The valve 112 further comprises at least one valve locking feature 160 for engagement with the stent locking feature 124. The valve locking feature 160 may be positioned on the inner surface 148 of the valve at or substantially near the distal end 142 of the valve. The locking feature 160 may, in some embodiments, be positioned in the valve channel 154. The locking feature 160 may, in some embodiments, be positioned on the outer surface 146 of the valve at or substantially near the distal end of the valve. The locking feature 160 as shown is a generally L-shaped flange having a first side 162 and a second side 164 longer than the first side 164. The second side 164 is positioned parallel to the outer surface 146 and the first side 162 is positioned perpendicular to the second side 164. In some embodiments, the locking feature 160 may incorporate a radiopaque marker or other imaging marker to assist with proper positioning of the valve at the repair site and/or the positioning of the valve relative to the stent. In at least the embodiment shown in FIG. 2, the locking wire 109 may be connected to the locking feature 160 at a distal end of the locking wire 109. The locking wire 109 may be connected at a proximal end to a handle assembly of the catheter for the operator to manipulate the locking wire 109 to pull the valve 112 into an engaged position with the stent 110. In some embodiments, the distal tip 103 may be expandable to a larger diameter, and when the guidewire is pulled proximally, the distal tip 103 pushes the valve 112 into an engaged position with the stent 110.

FIG. 3 shows the valve 112 in the engaged position with the stent 110, with the locking wires 109 still attached to the valve 112. In the engaged position with the stent 110, the valve body 140 is disposed within the stent lumen 122. In the engaged position, the valve cuff 152 may overlap a portion of the outer surface of the stent 110. Further, in the engaged position, the distal end 114 of the stent 110 may be positioned within the valve channel 154. As shown in FIG. 3, the valve body 140 is at least partially retained within the stent locking feature 124. The valve locking feature 160 is engaged with the stent locking feature 124 at a distal end of the locking channel 124. As shown the first side 162 of the valve locking feature 160 abuts the flanged portion 134 of the stent locking feature 124. The stent locking feature 124 may be a track, an opening within the framework of the stent or a strut of the stent, a guidewire, or another suitable element for aligning the valve and the stent in the engaged position. The valve locking feature 160 may lock into the stent locking feature 124 incrementally or in a stepped pattern, like a rack and pinion assembly or a ratcheting mechanism, to provide feedback to the operator on the position of the valve relative to the stent, or it may lock only once the valve 112 is in a fully engaged position. In some embodiments, engagement of the valve locking feature 160 with the stent locking feature 124 cuts, clips, releases, or otherwise disconnects the locking wires 109 from the valve assembly 100. This helps ensure that the valve 112 is fully engaged with the stent. Once the locking wires 109 are disconnected from the valve assembly 100, the catheter assembly 102—including the tip 103, the guidewire 105, the inner shaft 107, and the retractable sheath can be withdrawn.

Figure 4:
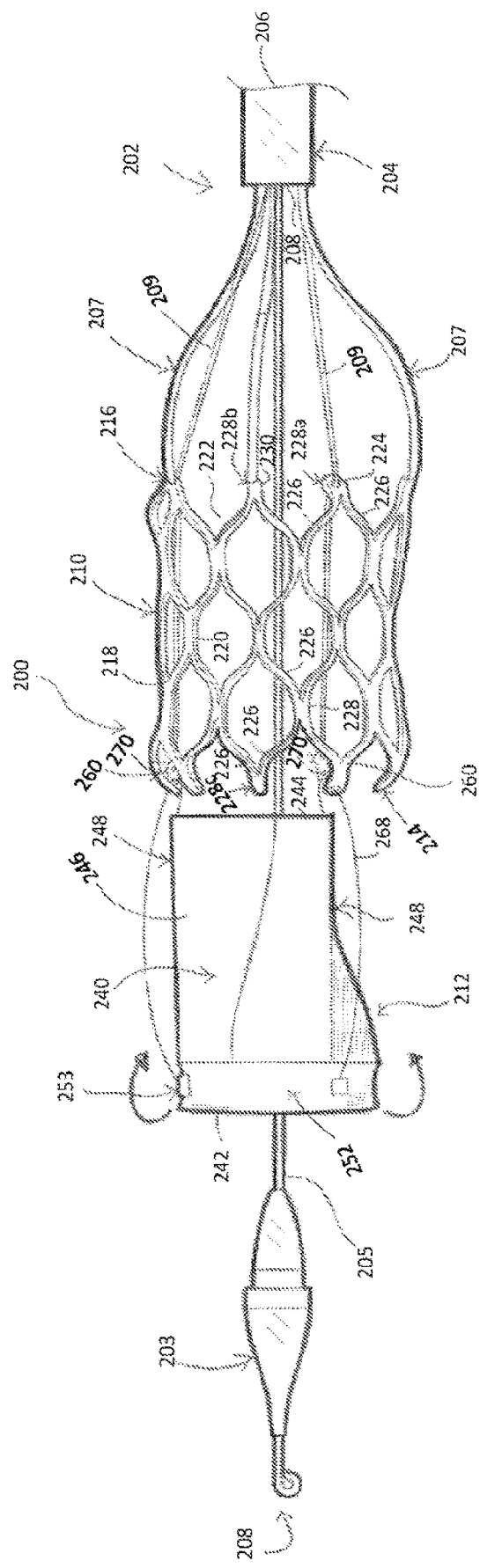
FIG. 4 is a side view of another embodiment of a replacement heart valve assembly in an expanded position.
Figure 5:
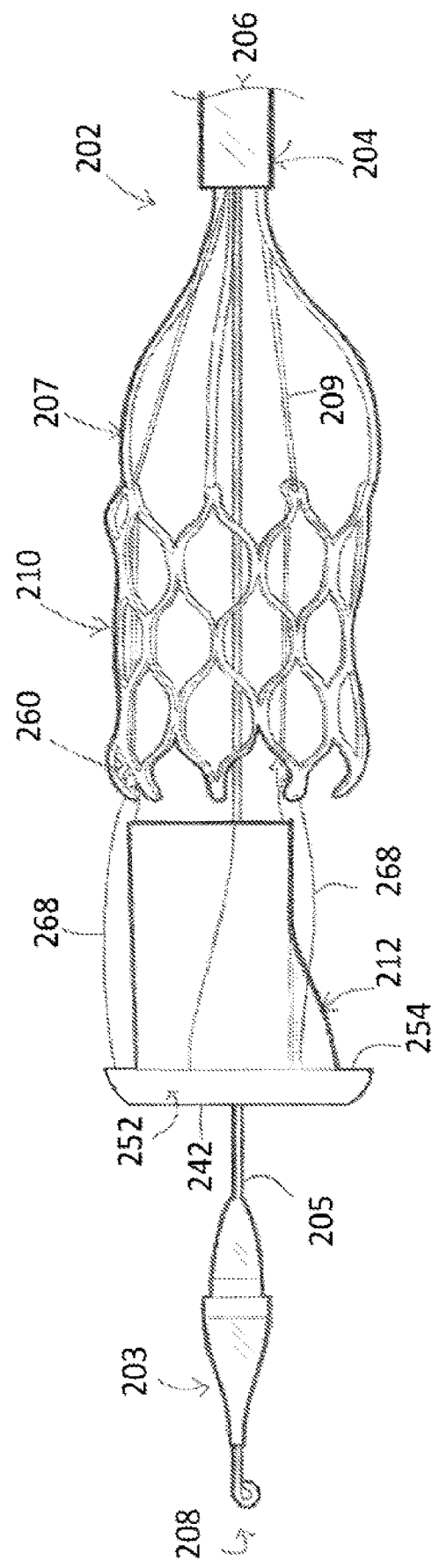
FIG. 5 is a side view of the replacement heart valve assembly of FIG. 4 in a partially deployed position.
Figure 6:
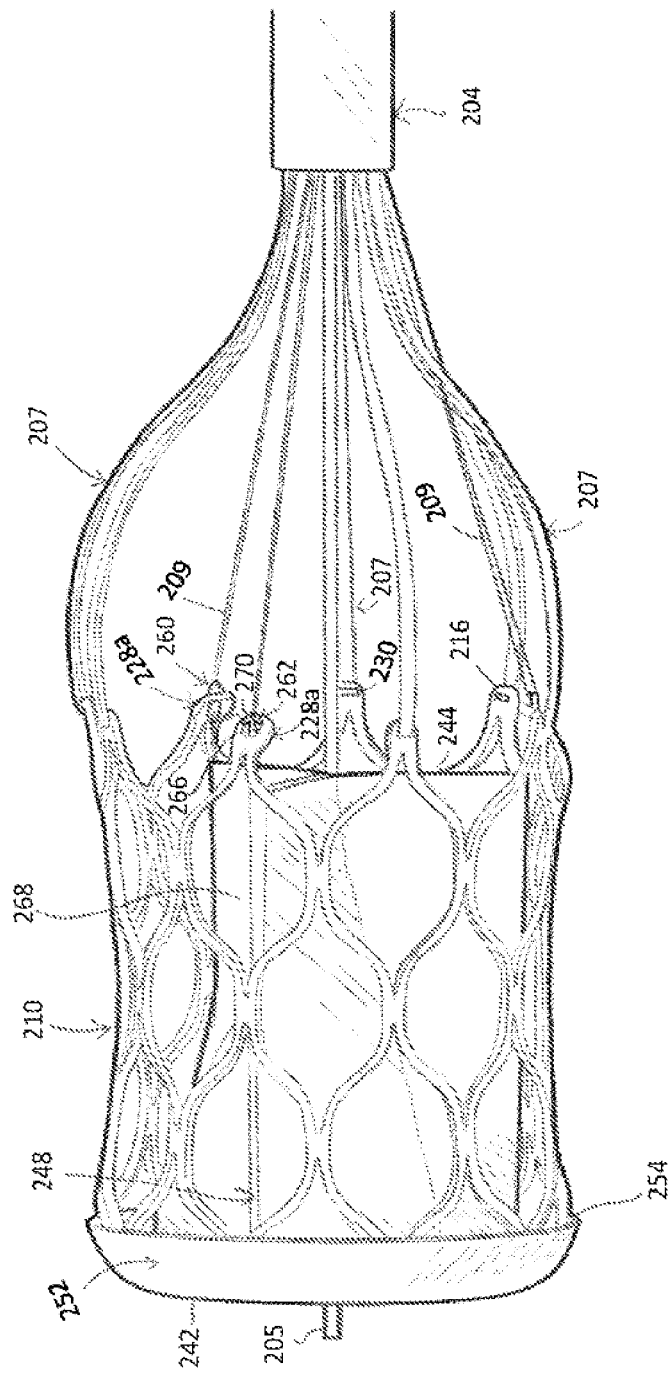
FIG. 6 is a side view of the replacement heart valve assembly of FIG. 5 in a fully deployed position, with the valve in an engaged position with the stent of the replacement heart valve assembly.

FIGS. 4-6 show another embodiment of the present disclosure. FIG. 4 shows a valve assembly 200, which comprises a stent 210 and a valve 212 disposed distally of the stent 210, and a catheter assembly 202. FIG. 4 shows the valve assembly 200 in an expanded position.

The stent 210 has a distal end 214, a proximal end 216, an outer surface 218 extending between the distal end 214 and the proximal end 216, and an inner surface 220 extending between the distal end 214 and the proximal end 216 and defining a stent lumen 222 therein. At least at the proximal end 216, the stent 210 comprises at least one stent locking feature 224 for engagement with a locking feature of the valve. As shown in FIG. 4, the stent 210 comprises a plurality of connected struts 226 which connect at nodes 228. At least at the proximal end 216 of the stent 210, some pairs of circumferentially adjacent struts 226a are attached at locking end nodes 228a and other pairs of circumferentially adjacent struts 226b are attached at gripping end nodes 228b. Still other pairs of circumferentially struts at either end of the stent 210 may form end nodes 228c. Each locking end node 228a has a stent locking feature 224 for engagement with a locking feature of the valve 212. As shown in FIG. 4, the stent locking feature 224 is a hole within the locking end node 228a. In other embodiments, the stent locking feature 224 may be a plurality of slots or other openings within the locking end node 228a. As shown in FIG. 4, the locking end node 228a is bent inwardly towards the stent lumen 222 at an angle. In at least one embodiment, the locking end node 228a is bent inwardly between about 10 degrees and 60 degrees relative to the outer surface 218 of the stent. In at least one embodiment, the locking end node 228a is bent inwardly between about 25 degrees and 50 degrees. In at least one embodiment, the end node 228a is bent inwardly between about 35 degrees and 50 degrees. In at least one embodiment, the locking end node 228a is bent inwardly between about 40 degrees and 50 degrees. In at least one embodiment, the locking end node 228a is bent inwardly at an angle of 45 degrees. In at least one embodiment, there are the same number of locking end nodes 228a at the distal end 226 as there are valve commissures on valve 212. As shown in FIG. 4, each gripping end node 228b has a stent gripping feature 230 for engaging with the catheter assembly 202. In at least the embodiment shown in FIGS. 4-6, the stent gripping feature 230 is a slot extending between the outer surface of the stent and the inner surface of the stent. In other embodiments, the stent gripping feature 230 may comprise a channel having a depth less than the thickness of the end node, at least one bump on a surface of the stent, at least one hole, or combinations thereof. In at least one embodiment, the stent gripping feature 230 may comprise a claw-like element at the proximal end of the node 228b. In at least one embodiment, the gripping end node 228b is bent inwardly towards the stent lumen 222 at an angle. In at least one embodiment, the gripping end node 228b is bent inwardly towards the stent lumen 222 at an angle less than the angle of the locking end nodes 228a.

As shown in FIG. 4, the valve 212 comprises a valve body 240 defining a distal end 242, a proximal end 244, an outer surface 246 extending between the distal end 242 and the proximal end 244, and an inner surface (not shown) extending between the distal end 242 and the proximal end 244. The inner surface may define a valve lumen. At least one valve leaflet may be disposed with the valve lumen. The valve 242 may further comprise a number of commissures 248, which may or may not be equal to the number of valve leaflets of the valve 212. In at least one embodiment, the valve 212 may have three leaflets (not shown) and three commissures 248. The valve 212 may further comprise a cuff portion 252 near the distal end 242 of the valve body. In some embodiments, the cuff portion 252 may comprise a skirt. The cuff portion 252 defines a valve channel 254 between the cuff 252 and the outer surface 246 of the valve body 240. As shown in FIG. 4, the cuff portion 252 is inverted and extends distally from the valve body 240. The cuff portion 252 has a plurality of cuff connectors 253 on a surface of the cuff portion 252 within the valve channel 254. The cuff connectors 253 may be rigid elements connected to the cuff portion 252, such as with sutures or other means. The cuff connectors 253 may be formed from a material other than the tissue used for the valve 212. The valve 212 further comprises at least one valve locking feature 260 for engagement with stent locking feature 224. As shown in FIG. 4, the valve locking feature 260 comprises an arrow 262 having a point 264 and a shaft 266. In at least the embodiment shown, the point 264 is positioned proximally from the shaft 266. In other embodiments, the point 264 is positioned distally from the shaft 266. In at least one embodiment, the arrow 262 comprises a material different than the stent 210. The valve locking feature 260 further comprises a tether 268 connecting the arrow 262 to the valve 212. The tether 268 may be connected at one end to at least one cuff connector 253. In some embodiments, the tether 268 may be threaded through a hole 270 on the arrow 262 and connected at another end to the inner surface of the valve 212. In some embodiments, the tether 268 may be connected at the other end to a second cuff connector 253 circumferentially adjacent to the first connector. In some embodiments, the locking feature 260 may comprise a double arrow with two arrows 262 connected longitudinally to one another. In other embodiments, instead of an arrow, the locking feature 260 may comprise a ball also connected to a tether in a similar arrangement.

As shown in FIG. 4, the catheter assembly 202 has a retractable sheath 204 with a proximal end 206 and a distal end 208. The catheter assembly 202 may further comprise a tip 203 near the distal end 208 and a guidewire 205 with the retractable sheath 204. The catheter assembly 202 may further comprise one or more gripping fingers 207 to assist with positioning, recapturing, and/or repositioning of the valve assembly 200. As shown in FIG. 4, the gripping fingers 207 are engaged with the gripping feature 230 of the stent 212. The catheter assembly 202 may further comprise at least one locking wire 209 connected to the valve assembly 200 for pulling the valve 212, in the expanded position, in a proximal direction towards the stent 210 also in an expanded position to connect the stent 210 to the valve 212. As shown in FIG. 4, the catheter assembly 202 has at least two locking wires 209, or at least one locking wire 209 for each valve commissure, although it is contemplated by this disclosure that any number of locking wires 209 may be suitable to control the engagement of the valve 212 with the stent 210. In some embodiments, the at least one locking wire 209 is connected to the valve locking feature 260. In at least the embodiment shown in FIG. 4, the at least one wire 209 is looped through the stent locking feature 230, through a hole in the valve locking feature 260, and back through the locking feature 230.

With a force applied to the locking wires 209 in a proximal direction, the locking wires 209 pull on the valve locking features 260, which in turn pulls on the tethers 268 to flip the cuff portion 252 from its inverted position to its deployed position. FIG. 5 shows the assembly in a partially deployed position with the cuff portion 252 in its deployed position and defining valve channel 254. With additional force applied to the locking wires 209 in a proximal direction, the arrows 262 of the valve locking features 260 are pulled proximally until they pierce through the relative stent locking feature 230 into the engaged position. In this position, the point 264 is proximal of the stent 210 and the shaft 266 extends through the hole of the stent locking feature 230. The valve 212 is then locked to the stent 210 in the engaged position as shown in FIG. 6. The distal end 214 of the valve is positioned within the valve channel 254 in the engaged position. Even in the engaged position shown in FIG. 6, the valve assembly 200 can be recaptured and then redeployed in some embodiments. In at least one embodiment, pushing the retractable sheath distally in a first direction will at least partially resheath the valve assembly 200 which can be repositioned in the vasculature. Once repositioned, in at least one embodiment, pulling the retractable sheath proximally in a second direction will allow the valve assembly to self-expand into the deployed position with the stent engaged with the valve. The gripping fingers 207 may be released from the gripping feature 230 by pushing distally on the gripping fingers to increase the deflection in the gripping finger 207 until the gripping finger 207 is no longer engaged with the gripping feature 230.

Once the deployed valve assembly 200 is in a desired position within the vasculature, the locking wires 209 can be released from the valve locking features 260. In at least one embodiment, each locking wire 209 has a first end and a second end, and the locking wire is looped through the a hole in the valve locking feature 260. Each end of the locking wire 209 may be positioned proximally from the proximal end of the valve assembly. At least one of the ends may be connected to the catheter handle or to another portion of the catheter assembly proximally from the deployed valve assembly. At least one of the ends may be released, and the released end of the locking wire 209 can be pulled proximally through the hole in the valve locking feature 260 and withdrawn along with the catheter assembly. In other embodiments, to allow the locking wires 209 to be released from the deployed valve assembly 200, the locking wires 209 may have a detachment point that, when a sufficient force is applied to the locking wire 209 in a proximal direction, the locking wire 209 separates into two pieces, both attached to the catheter assembly, and can be withdrawn with the catheter assembly. In still other embodiments, the valve locking feature 260 may include a releasing element that clips the locking wire 209 when a sufficient force is applied to the locking wire in a proximal direction.

In the deployed position, the valve locking features 260 remain engaged with the relative stent locking feature 230 under tension and positioned at an inward angle relative to the outer surface of the stent. As a result, the valve locking feature 260, and more specifically the tether 268, acts as a shock absorber for the valve assembly. The pressures involved with the opening and closing of the valve leaflets puts significant forces on the commissures of the valve. The engagement of the valve locking features 260 with the stent locking feature 230 assist with dissipation of those forces.

In at least one embodiment, the valve assembly may be packaged in a sterilized packaging system. More specifically, the valve assembly can be packaged with at least a portion of the catheter assembly in the packaging system as described in the disclosure of U.S. Patent Provisional App. Ser. No. 62/533,429 filed on Jul. 17, 2017 and entitled "Sterilized Packaging System For Catheter," which is incorporated by reference herein in its entirety. As described therein, the packaging system may comprise a tray with a plurality of chambers. At least the valve of the valve assembly may be positioned in one chamber of the tray, and the chamber may contain a volume of a sterilizing fluid such as a sterilant. Thus, the valve may be packaged "wet" and may have a first diameter while packaged. In some embodiments, when the valve assembly is removed from the chamber, the valve may shrink (either through mechanical means or the material properties of the valve) and have a second diameter less than the first diameter. The valve assembly may then be pulled proximally through a sheath of the catheter assembly to position the valve assembly within the catheter assembly in the delivery position shown, for example, in FIG. 1. Once the sheath is retracted within the vasculature and the valve is exposed to fluid within the body, the valve may self-expand to the first diameter. In some embodiments, the first diameter may be less than the diameter of the valve when the valve is in the expanded position shown, for example, in FIG. 2.

Although the above disclosure describes a valve assembly comprising both the valve and a stent, it is contemplated by this disclosure that embodiments of this invention may include a valve that is not attached to a stent.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for the devices described herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

While the systems and methods described herein have been described in reference to some exemplary embodiments, these embodiments are not limiting and are not necessarily exclusive of each other, and it is contemplated that particular features of various embodiments may be omitted or combined for use with features of other embodiments while remaining within the scope of the invention. Any feature of any embodiment described herein may be used in any embodiment and with any features of any other embodiment.

What is claimed is:

1. A system for endovascular heart valve repair, the system comprising:
    a delivery catheter comprising a retractable sheath and an inner shaft coaxial with the retractable sheath;
    a valve assembly having a delivery position and an expanded position, the valve assembly comprising:
        a stent having a proximal end and a distal end, the stent having an outer surface and an inner surface defining a stent lumen, the stent having at least one stent locking element; and
        a valve having a proximal end and a distal end, the valve having an outer surface and an inner surface defining a valve lumen, the valve further comprising at least one valve leaflet within the valve lumen, a valve body extending from the proximal end and the distal end, a cuff at the distal end of the valve and defining a valve channel between the cuff and the outer surface of the valve body, and at least one valve locking feature for engagement with the stent locking element, wherein the valve locking feature is positioned within the valve channel;
    wherein, when the valve assembly is in the delivery position, the valve assembly is disposed between the retractable sheath and the inner shaft, and the proximal end of the valve is positioned distally from the distal end of the stent.

2. The system of claim 1, wherein, when the valve assembly is in an expanded position, the valve is moved in a proximal direction into the stent lumen until the valve locking feature is engaged with the stent locking element and the distal end of the stent is positioned within the valve channel.

3. The system of claim 1, further comprising at least one cable wire disposed between the retractable sheath and the inner shaft.

4. The system of claim 3, wherein a distal end of the at least one cable wire is connected to the valve.

5. The system of claim 3, wherein the at least one cable wire is connected to the distal end of the valve.

6. The system of claim 3, wherein the at least one cable wire is connected to the valve locking feature.

7. The system of claim 3, wherein when the valve locking feature is engaged with the stent locking element, the at least one cable wire is disconnected from the valve.

8. The system of claim 3, wherein the at least one cable wire has a detachment point between the distal end of the at least one cable wire and the proximal end of the at least one cable wire.

9. A system for endovascular heart valve repair, the system comprising:
    a delivery catheter comprising a retractable sheath and an inner shaft coaxial with the retractable sheath;
    a valve assembly having a delivery position and an expanded position, the valve assembly comprising:
        a stent having a proximal end and a distal end, the stent having an outer surface and an inner surface defining a stent lumen, the stent having at least one stent locking element; and
        a valve having a proximal end and a distal end, the valve having an outer surface and an inner surface defining a valve lumen, the valve further comprising at least one valve leaflet within the valve lumen, a valve body extending from the proximal end and the distal end, a cuff at the distal end of the valve and defining a valve channel between the cuff and the outer surface of the valve body, and at least one valve locking feature for engagement with the stent locking element; and
    at least one cable wire disposed between the retractable sheath and the inner shaft, wherein the at least one cable wire is connected to the valve locking feature;
    wherein, when the valve assembly is in the delivery position, the valve assembly is disposed between the retractable sheath and the inner shaft, and the proximal end of the valve is positioned distally from the distal end of the stent.

10. The system of claim 9, wherein, when the valve assembly is in an expanded position, the valve is moved in a proximal direction into the stent lumen until the valve locking feature is engaged with the stent locking element and the distal end of the stent is positioned within the valve channel.

11. The system of claim 9, wherein when the valve locking feature is engaged with the stent locking element, the at least one cable wire is disconnected from the valve.

12. The system of claim 9, wherein the at least one cable wire has a detachment point between the distal end of the at least one cable wire and the proximal end of the at least one cable wire.

13. The system of claim 9, wherein the valve locking feature is positioned within the valve channel.

* * * * *